(12) United States Patent
Erbs

(10) Patent No.: US 11,179,487 B2
(45) Date of Patent: *Nov. 23, 2021

(54) METHOD AND APPARATUS FOR SANITATION OF ICE PRODUCTION AND DISPENSING SYSTEM

(71) Applicant: Manitowoc Foodservice Companies, LLC, New Port Richey, FL (US)

(72) Inventor: Daryl Gregory Erbs, Tarpon Springs, FL (US)

(73) Assignee: MANITOWOC FOODSERVICE COMPANIES, LLC, New Port Richey, FL (US)

( * ) Notice: Subject to any disclaimer, the term of this patent is extended or adjusted under 35 U.S.C. 154(b) by 200 days.

This patent is subject to a terminal disclaimer.

(21) Appl. No.: 16/281,863

(22) Filed: Feb. 21, 2019

(65) Prior Publication Data

US 2019/0175773 A1 Jun. 13, 2019

Related U.S. Application Data

(63) Continuation of application No. 15/185,979, filed on Jun. 17, 2016, now Pat. No. 10,300,161.
(Continued)

(51) Int. Cl.
*A61L 2/18* (2006.01)
*F25C 5/00* (2018.01)
*F25C 1/00* (2006.01)

(52) U.S. Cl.
CPC .............. *A61L 2/183* (2013.01); *F25C 1/00* (2013.01); *F25C 5/00* (2013.01); *A61L 2202/17* (2013.01);
(Continued)

(58) Field of Classification Search
CPC ........ A61L 2/183; A61L 2202/17; F25C 1/00; F25C 1/22; F25C 1/24; F25C 1/243; F25C 1/246; F25C 2300/00; F25C 2400/12
See application file for complete search history.

(56) References Cited

U.S. PATENT DOCUMENTS 5,289,691 A * 3/1994 Schlosser ............... A23G 9/228
62/303
6,167,711 B1 * 1/2001 Slattery ................... A61L 2/202
62/344
(Continued)

FOREIGN PATENT DOCUMENTS

JP 2014505232 A 2/2014
WO 2005100257 A1 10/2005
WO 2012109436 A1 8/2012

OTHER PUBLICATIONS

Extended European Search Report dated Jan. 22, 2019 for European application No. 16812544.1.
(Continued)

*Primary Examiner* — Jianying C Atkisson
*Assistant Examiner* — Miguel A Diaz
(74) *Attorney, Agent, or Firm* — Ohlandt, Greeley, Ruggiero and Perle, LLP

(57) ABSTRACT

An ice maker includes an ice making unit comprising an evaporator connected to a refrigeration system, an ice holding bin, a sump, a pump, a drain valve, an ozonated water source, and a controller. The controller activates the ozonated water source supplying a first volume of ozonated water to the sump, thereafter activates the pump to circulate the first volume of ozonated water from the sump to the ice making unit, once a predetermined sterilization time has been reached, the controller turns off the pump and drains the first volume of ozonated water from the sump. The controller initiates an ice making mode, and activates the ozonated water source to supply a second volume of ozonated water to the sump, thereafter activates the pump to circulate the second volume of ozonated water from the sump to the ice making unit forming ozonated ice on the evaporator, and initiates an ice harvest mode to remove the
(Continued)

ozonated ice from the evaporator and delivers it to the ice holding bin.

2 Claims, 7 Drawing Sheets

Related U.S. Application Data

(60) Provisional application No. 62/182,173, filed on Jun. 19, 2015, provisional application No. 62/182,959, filed on Jun. 22, 2015.

(52) U.S. Cl.
CPC ...... *F25C 2300/00* (2013.01); *F25C 2400/12* (2013.01)

(56) References Cited

U.S. PATENT DOCUMENTS

| | | |
|---|---|---|
| 6,334,328 B1 | 1/2002 | Brill |
| 6,506,428 B1 | 1/2003 | Berge et al. |
| 7,029,587 B2 | 4/2006 | Andrews |
| 9,803,907 B2 | 10/2017 | Erbs et al. |
| 2005/0103726 A1* | 5/2005 | Palm .................. C02F 1/78 210/760 |
| 2007/0214809 A1* | 9/2007 | DiLorenzo .............. F25C 1/18 62/66 |
| 2012/0031114 A1* | 2/2012 | Mueller ................ G01F 23/24 62/66 |
| 2012/0198870 A1 | 8/2012 | Erbs et al. |

OTHER PUBLICATIONS

Chinese Office Action dated Apr. 16, 2020 for Chinese Application No. 201680035974.0.
Chinese Office Action (English translation) with Search Report dated Jun. 25, 2019 for Chinese application No. 201680035974.0.
Japanese Office Action dated Feb. 5, 2019 for Japanese application No. 2017-565767.
International Search Report dated Sep. 7, 2016 for PCT international application No. PCT/US2016/038133.
Written Opinion Report dated Sep. 7, 2016 for PCT international application No. PCT/US2016/038133.
Korean Office Action dated Dec. 9, 2019 for Korean Application No. 10-2017-7032789; 7 pgs.

* cited by examiner

METHOD AND APPARATUS FOR SANITATION OF ICE PRODUCTION AND DISPENSING SYSTEM

CROSS REFERENCE TO RELATED APPLICATIONS

The present application is a continuation of U.S. patent application Ser. No. 15/185,979, filed on Jun. 17, 2016, which in turn claims the benefit of U.S. Provisional Patent Application No. 62/182,173, filed on Jun. 19, 2015, and U.S. Provisional Patent Application No. 62/182,959, filed on Jun. 22, 2015, each of which is incorporated herein by reference.

BACKGROUND OF THE DISCLOSURE

1. Field of the Disclosure

The present disclosure relates generally to ice makers. More particularly, the present disclosure relates to an apparatus and method for sanitizing an ice maker.

2. Description of Related Art

Commercial ice makers and ice dispensers generally have a volume of space that contains the means for production, storage, and dispensing of ice that is intended for cooling of beverages or as an ingredient in a recipe. Since the ice will be consumed along with the beverage or food item, it is important that the ice is free from harmful organisms or other matter. The foodzone is intended to serve as a barrier against contamination of the ice that is produced and stored by airborne particles including dust, spores, and micro-organisms. However, it is well known that the foodzones in typical ice makers and dispensers are not completely sealed, allowing some ingress of particles and organisms into the foodzone over time. The normal practice to maintain acceptable levels of sanitation for the foodzone is to periodically clean and disinfect the foodzone using a combination of mechanical and chemical means. It is also known that some potable water supplied to the ice machine may contain some degree of contaminants. It is further known that if ice machines are not periodically and thoroughly cleaned in accordance with manufacturers' guidelines, harmful micro-organisms may grow or be introduced into various parts of the ice machine, such as the production zone or storage bin, potentially posing cleanliness concerns, particularly in high risk settings such as hospitals. Equipment cleaned according to standard cleaning protocols and schedules may not be sufficient to meet stringent, constant cleanliness requirements in such environments.

Accordingly, it has been determined by the present disclosure, there is a need for a method and system for automatically sanitizing the foodzone of an integrated ice maker and ice dispenser where the foodzone is either sealed from the surrounding airspace and machine compartments in the unit or is held under positive pressure using air or other gas that is free of particulate matter and micro-organisms. There is a further need for a means of maintaining a sanitary state for the foodzone without the need to open the foodzone, and disrupt the protection afforded by the sealing and/or pressurization mechanisms that provide protection against airborne contaminants entering the foodzone.

SUMMARY OF THE DISCLOSURE

In one embodiment, the present disclosure provides an ice maker comprising a refrigeration system, an evaporator in operable communication with the refrigeration system, a water sump, a water pump in communication with the water sump, a drain valve in communication with the water sump, a potable water line that supplies potable water to the water sump via a potable water supply valve, and an ozonated water line that supplies ozonated water to the water sump via an ozonated water supply valve. The potable water supply line and the ozonated water supply line are separate from one another. During a sanitization mode of operation of the ice maker, the ozonated water supply valve is open. During an ice-making mode of operation of the ice maker, the potable water supply valve is open, and the ozonated water supply valve is closed.

The above-described and other advantages and features of the present disclosure will be appreciated and understood by those skilled in the art from the following detailed description, drawings, and appended claims.

DETAILED DESCRIPTION OF THE DISCLOSURE

Figure 1:
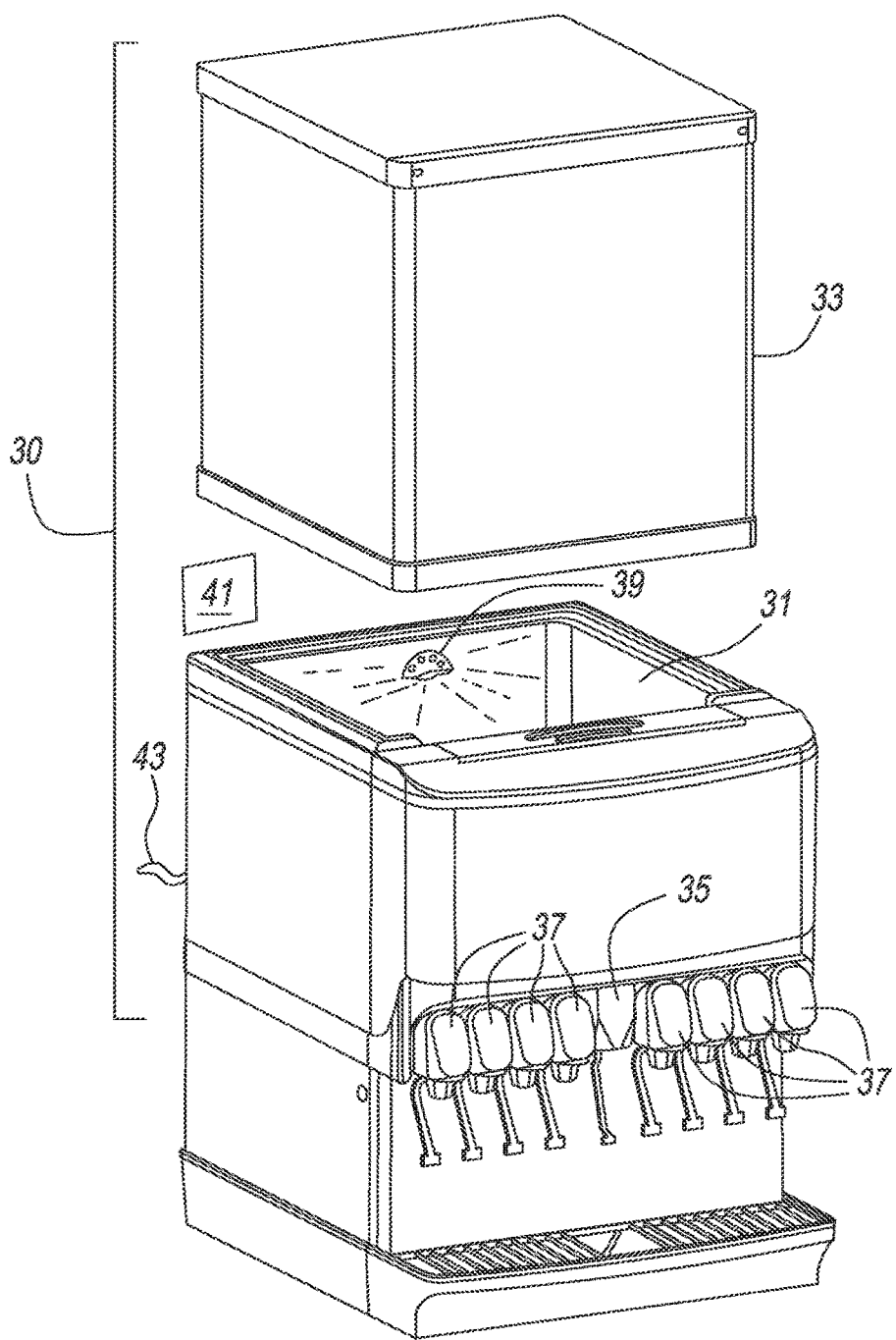
FIG. 1 provides a top, front perspective exploded view of an embodiment of an ice maker and bin assembly according to the present disclosure.

Referring to the drawings and in particular to FIG. 1, an exemplary embodiment of an ice maker of the present disclosure is generally referred to by 33. Ice maker 33 is connected to a bin 31 to form an ice maker and bin assembly 30. Ice is made in ice maker 33 and stored in bin 31. Ice stored in bin 31 can be selectively dispensed through an ice dispenser 35. Ice maker and bin assembly 30 may also incorporate conventional beverage dispensers 37.

Figure 2:
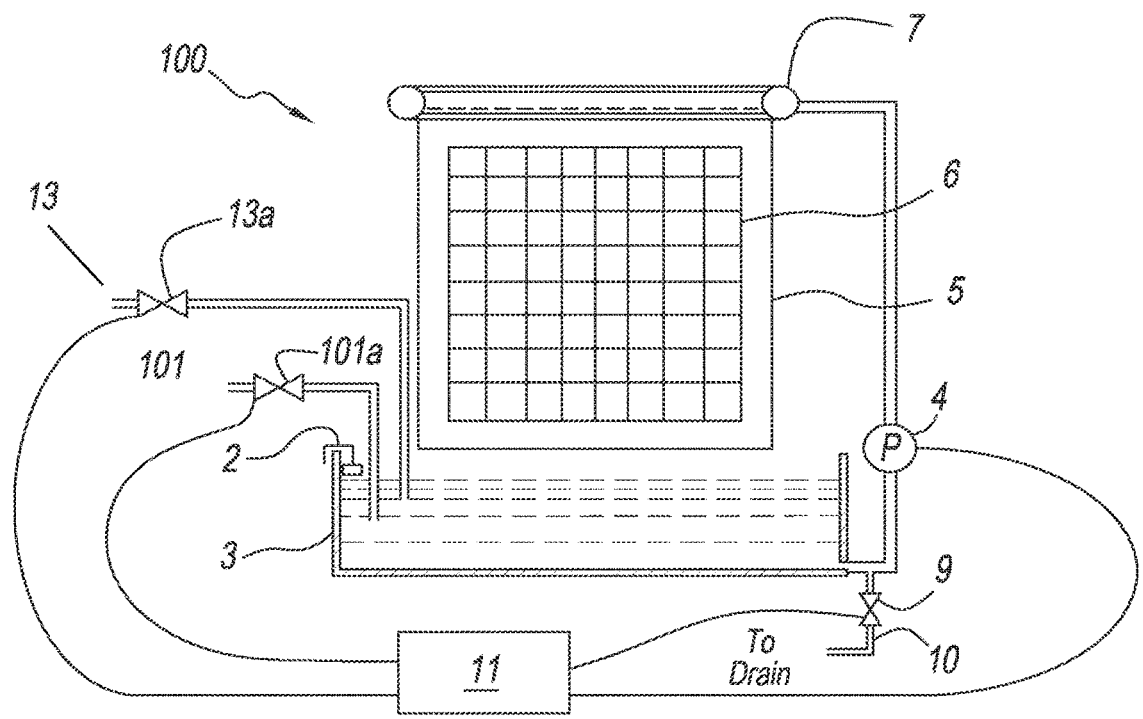
FIG. 2 provides a line diagram and drawing for an embodiment of a water/ice system of the ice maker and bin assembly of FIG. 1 having an ozonated water supply.

Referring to FIG. 2, ice maker 33 has a water/ice system 100. In a freeze cycle during normal operation, potable water supply 13 provides a source of potable water, normally tap water or tap water which has optionally been treated by filtration, ion exchange or the like to improve its quality. Attached lines control and direct the flow of water from the water supply 13 to flow into sump 3. Potable water supply 13 has a water supply valve 13A that supplies water to sump 3 in an open position and blocks supply of water to sump 3 in a closed position.

Sump 3 is equipped with a level controller 2, a drain valve 9, a drain line 10, and is connected and supplies a water supply to a suction side of a pump 4. Pump 4 circulates water from sump 3 to a distributor 7, where the water is directed over an evaporator plate 6 (also called the ice-forming mold or ice tray). Evaporator plate 6 is cooled by a conventional refrigeration system including a compressor, condenser and evaporator (not shown) when the refrigeration system is activated to form ice on evaporator plate 6. When the refrigeration system is deactivated, ice is not formed on evaporator plate 6. The water from the distributor 7 is directed across the evaporator plate 6 and, if not frozen to form ice on a first pass, is collected by a water curtain 5. This collected water is allowed to flow down the water curtain into the water sump or water reservoir 3, where it is collected and again circulated by the circulating pump 4 to the distributor 7 and recycled across evaporator plate 6 during a freezing cycle. The drain valve 9 may be activated by a solenoid valve to drain the water in sump 3.

In a harvest cycle during normal operation, coolant no longer is pumped through the evaporator of the refrigeration system. Instead, a hot gas solenoid valve (not shown) is opened in the refrigeration system in a conventional manner to route hot vaporous refrigerant from the compressor to the evaporator through a discharge line and bypass line, thereby heating up the evaporator plate 6. This causes the ice to release from the evaporator plate 6.

Water/ice system 100 has an ozonated water supply 101 for use during a sanitizing process. Ozonated water supply 101 has an ozonated water supply valve 101A that supplies ozonated water to sump 3 in an open position and blocks supply of water to sump 3 in a closed position.

Water/ice system 100 has a controller 11 that moves potable water supply valve 13A between the open position and the closed position. Controller 11 moves ozonated water supply valve 101A between the open position and the closed position. Controller 11 activates pump 4 to generate a flow of liquid, ozonated water or water that is not treated with ozone (also referred to as potable water), to distributor 7 and deactivates pump 4 so that liquid does not flow to distributor 7. Controller 11 moves drain valve 9 between the open position that drains liquid, ozonated water or potable water, from sump 3 and the closed position that maintains the liquid in sump 3. Controller 11 may have a memory and a processor to execute a program stored in the memory to operate ice maker 33 during normal operation and during a sanitizing process as well as a user interface to control operation of ice maker 33.

Figure 3:
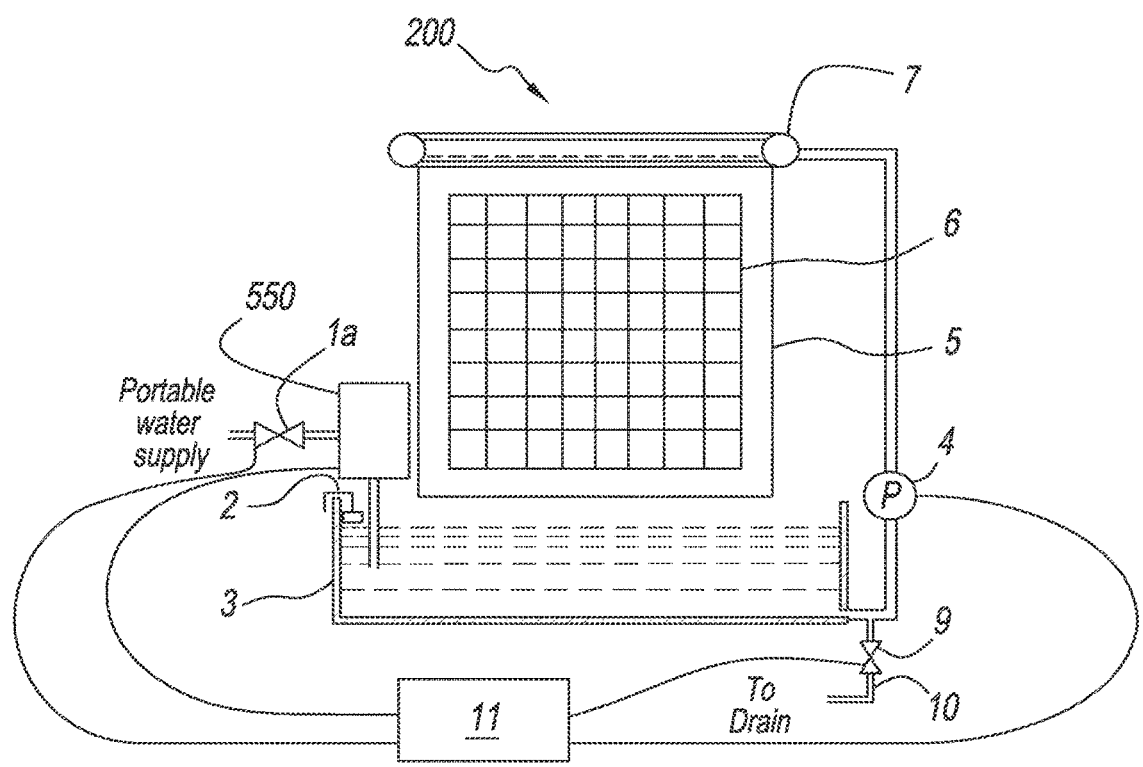
FIG. 3 provides a line diagram and drawing for an embodiment of a water/ice system of the ice maker and bin assembly of FIG. 1 having a water supply and an ozone generator.

FIG. 3 shows water/ice system 200. Water/ice system 200 is the same as water/ice system 100, however, water/ice system 200 has an ozone generator 550 that may be activated to incorporate ozone into water of potable water supply 1, which replaces ozonated water supply 101 of water/ice system 100.

Figure 3A:
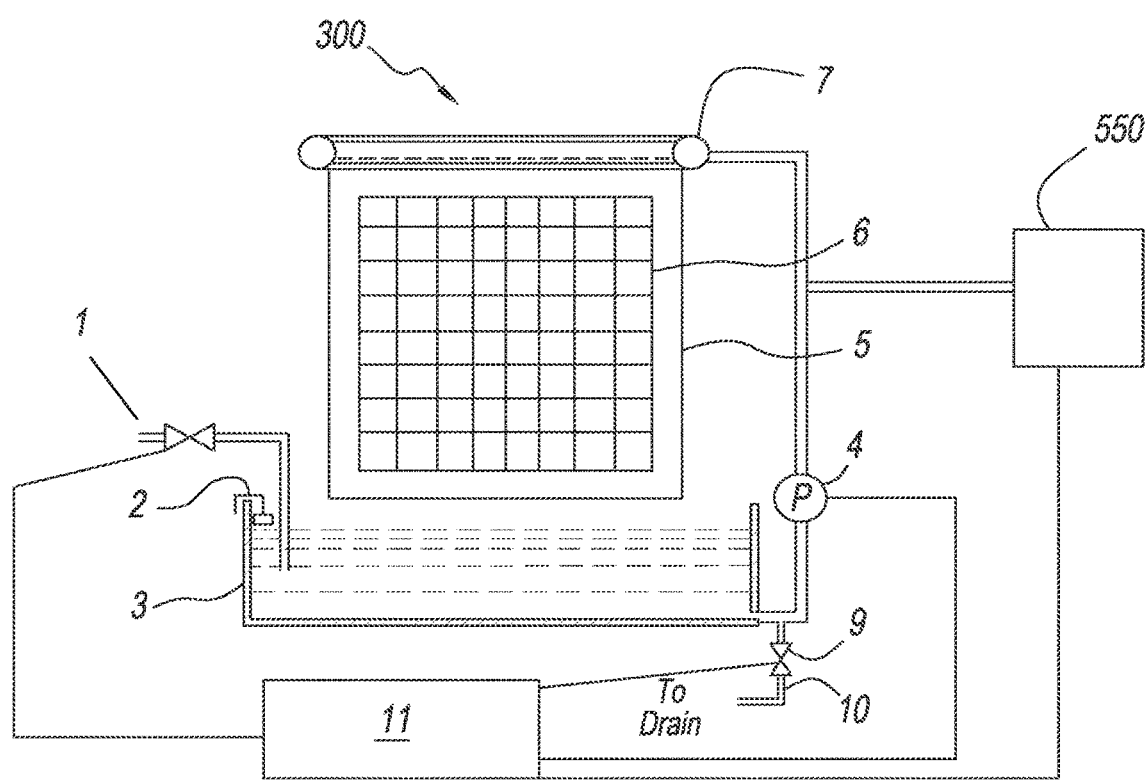
FIG. 3a provides a line diagram and drawing for an embodiment of a water/ice system of the ice maker and bin assembly of FIG. 1, having a water supply and an ozone generator in a different location than that of FIG. 3.

In FIG. 3a, water/ice system 300 is shown. System 300 has all of the same components as those in systems 100 and 200, with the following exceptions. In system 300, ozone generator is located and injects ozone into the water stream or a fluid line at a point between pump 4 and distributor 7. There are several advantages to placing generator 550 at this point. When ozone is generated, as discussed in greater detail below, it bubbles off of an anode in the generator. When water carrying this ozone is immediately directed into a sump, as in system 200, the ozone may bubble off into the air within the system. As discussed elsewhere in the present specification, this may have some advantages for cleaning and sanitizing purposes. However, if it is desired to keep as much of the ozone as possible within the water stream, introducing it at a point between pump 4 and distributor 7 helps achieve this goal, since the system is sealed at this point. In addition, the flow of the water between pump 4 and distributor 7 is typically higher and more turbulent than at other points in the system. This means that the ozone introduced by generator 550 at this point will dissolve more quickly, and can be added in a lower concentration than at other locations in the system.

Figure 4:
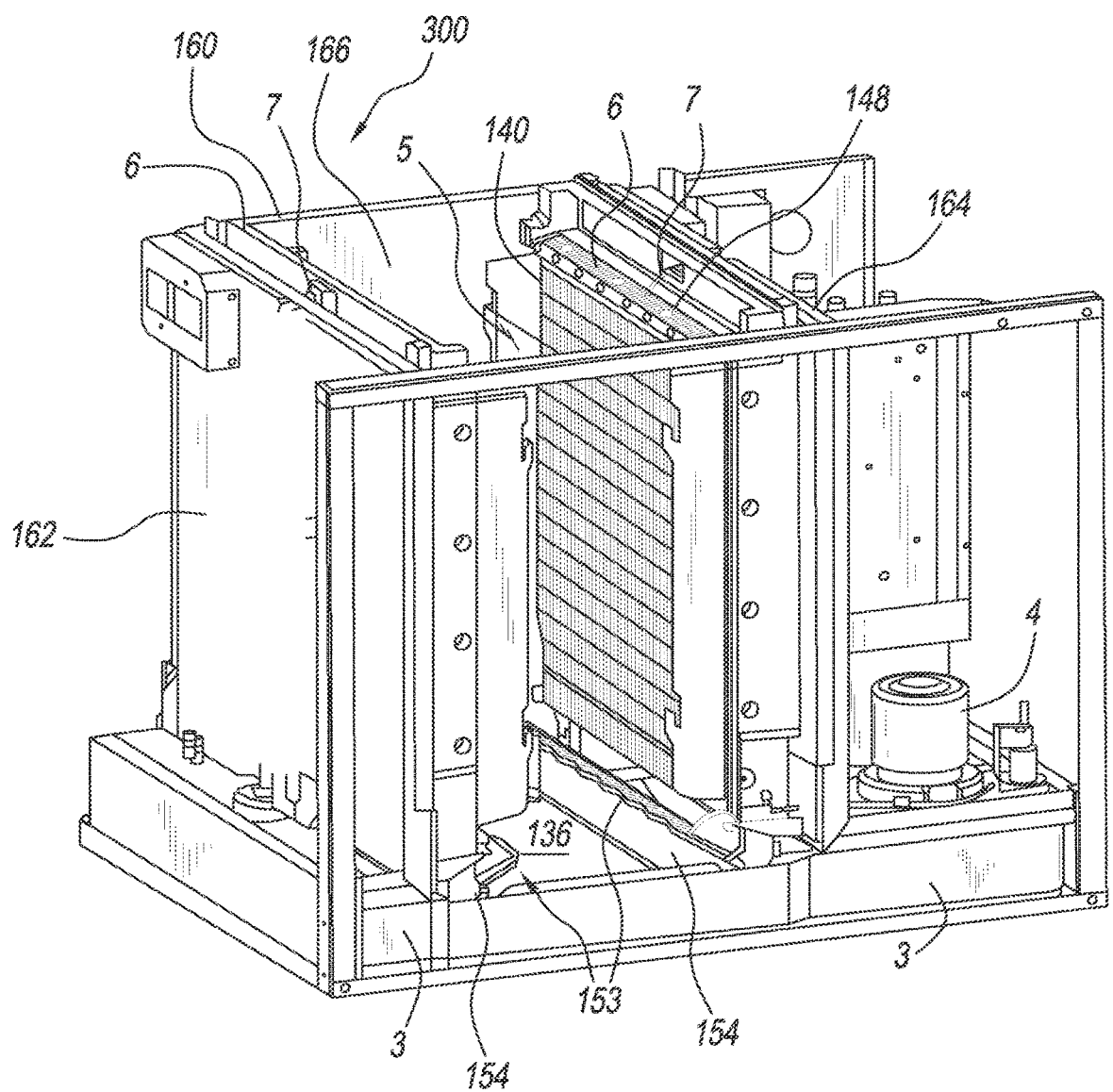
FIG. 4 is a top, front perspective view of an ice maker with parts removed for sake of clarity for use with the ice maker and bin assembly of FIG. 1.

Referring to FIG. 4, ice maker 33 may incorporate water/ice system 100 into an ice maker assembly 300 that has a pair of evaporator plates 6, distributors 7, pump 4, sump 3, and an ice chute 136 through which ice is discharged to bin 31 for collection and storage. Although ice maker assembly 300 illustrated in FIG. 4 is adapted for forming a geometric grid of cubes connected by a thin bridge layer of ice, it should be noted that the various aspects can be applied to ice machines adapted to produce ice in any other shape formed in unconnected or connected assemblies on any type of ice forming surface (e.g., individual pockets or other receptacles, one or more troughs, a flat or substantially flat ice forming sheet, and the like). With reference again to the embodiment of FIG. 4, each evaporator plate 6 of the illustrated ice maker assembly 300 includes an ice-forming surface 140. An evaporator 148 that is a part of the conventional refrigeration system is connected to each evaporator plate 6 to cool evaporator plate 6 when the refrigeration system is activated. An ice barrier 153 is positioned at the bottom of evaporator 6 along a boundary wall 154 separating sump 3 and ice chute 136. The ice barrier 153 is rotatably mounted, and is movable about a pivot axis between a first orientation, as shown in FIG. 4, and a second orientation. In the first orientation, liquid that contacts ice barrier 153 is directed into sump 3. When ice falls upon ice barrier 153, for example, during the harvest cycle, ice barrier 153 rotates by a force applied by an impact of the ice to rotate to the second position directed ice away from sump 3 and onto ice chute 136.

A foodzone is established by a rear wall 160, side walls 162, 164, a front wall (not shown) that contacts side walls 162, 164, and a top wall (not shown) that contacts rear wall 160, side walls 162, 164 and the front wall enclosing an interior volume 166. The term "foodzone" means the areas inside of the ice-making machine that are contacted by ice made by the machine, or by water that is converted into ice or splashes onto ice made by the machine. The foodzone also includes the space where air readily circulates that comes into contact with the surfaces that are used to form ice or contact water used to form ice.

Figure 5:
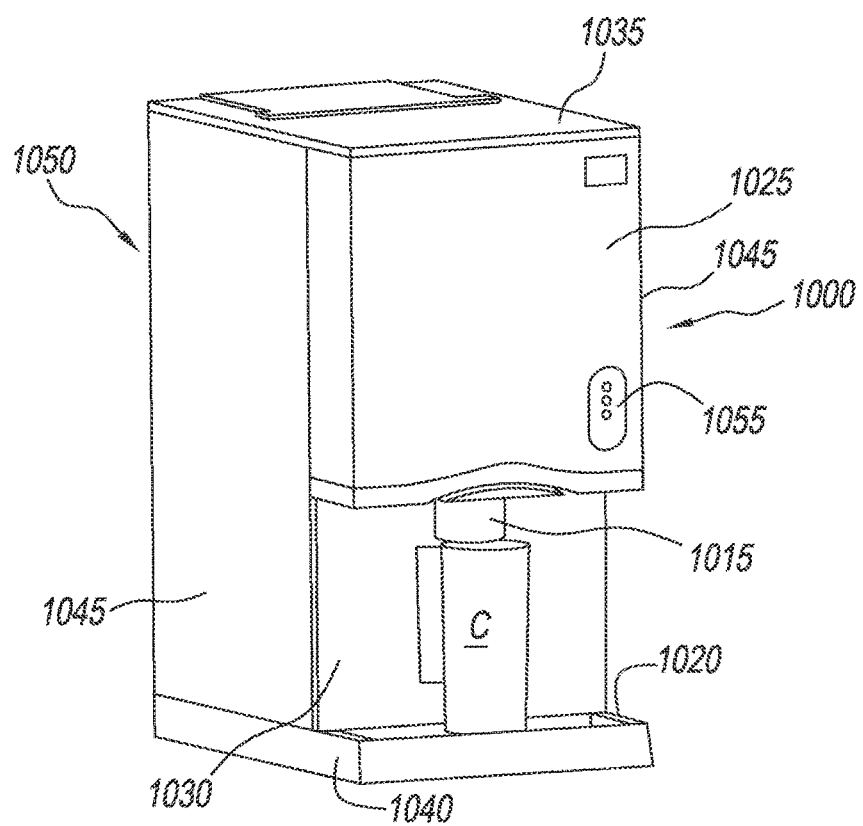
FIG. 5 provides a top, front perspective view of a continuous ice maker with integrated bin and dispenser according to the present disclosure.
Figure 6:
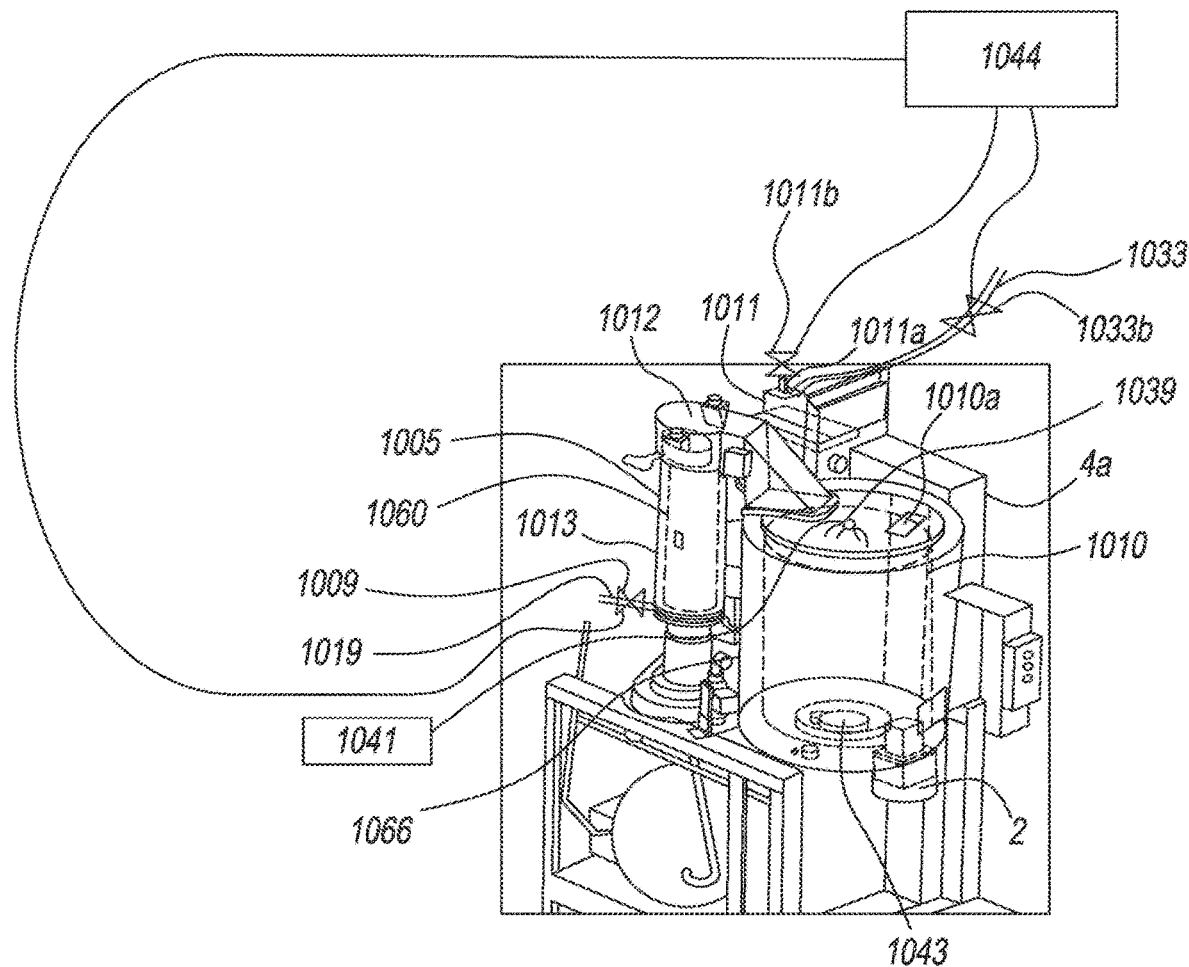
FIG. 6 is a top, front perspective view of the continuous ice maker of FIG. 5 with parts removed for sake of clarity.

Alternately, the configuration shown in FIGS. 5 and 6 connects a continuous ice maker 1005 to bin 1010 to form an ice maker and bin assembly 1000. In FIG. 5, ice maker and bin assembly 1000 comprises ice dispenser opening 1015, tray 1020 for holding a cup C for receiving dispensed ice, a door 1025, front panel 1030, top panel 1035, base 1040, side panels 1045, back panel 1050 and user interface 1055. FIG. 6 shows ice maker and bin assembly 1000 with door 1025, side panels 1045, top panel 1035 and back panel 1050 removed. Behind front panel 1030 is located bin 1010 that supplies ice to ice dispenser opening 1015. In the embodiment shown in FIG. 6, bin 1010 is disposed against front panel 1030, but this configuration could of course be otherwise. Bin 1010 has lid 1010a covering it, and ice from an evaporator 1013 (ice chamber) in thermal communication with a refrigeration system is transported from evaporator 1013 through ice chute 1012 and lid 1010a to bin 1010. Water is supplied to evaporator 1013 via gravity from reservoir 1011, that has potable water supply 1011a and an ozonated water supply 1033 entering the top of reservoir 1011. Broken lines 1060 show portions of the insides of bin 1010, lid 1010a, reservoir 1011, ice chute 1012, and evaporator 1013, defining the food zone 1066.

Potable water supply 1011a has a potable water supply valve 1011b. A controller 1044 moves potable water supply valve 1011b between an open position and a closed position. Potable water supply 1011a supplies potable water to reservoir 1011 when potable water supply valve 1011b is in an open position and blocks supply of potable water to reservoir 1011 when potable water supply valve 1011b is in a closed position. Ozonated water supply 1033 has an ozonated water supply valve 1033b. Controller 1044 moves ozonated water supply valve 1033b between an open position and a closed position. Ozonated water supply 1033 supplies ozonated water to reservoir 1011 when ozonated water supply valve 1033b is in an open position and blocks supply of ozonated water to reservoir 1011 when ozonated water supply valve 1033b is in a closed position. Evaporator 1013 has a drain 1009 with a drain valve 1019. Controller 1044 moves drain valve 1019 between an open position and a closed position. Drain 1009 drains liquid when drain valve 1019 is in an open position and blocks liquid from draining out of evaporator 1013 when drain valve 1019 is in a closed position.

During normal operation of ice maker and bin assembly 1000, a heat exchange tube of a refrigeration system carrying the refrigerant is utilized for cooling the evaporator 1013. Controller 1044 moves potable water supply valve 1011b to the open position delivering potable water from reservoir 1011 to evaporator 1013. Drain valve 1019 is in a closed position. An auger is positioned in evaporator 1013 and includes a generally spiral-shaped auger flight. Evaporator 1013 is generally filled with potable water along a length of the auger so that the water adjacent to the wall of evaporator 1013 is frozen into ice crystals. Therefore, as the ice crystals are being formed, the rotating auger flight scrapes the layer of ice from the inner surface and transports the newly-formed ice flakes in the upward direction. A nugget forming device may be positioned at the top portion of the auger to compact the ice by forcing the ice through generally small extrusion orifices. The compacted ice is then cut or broken into relatively small nuggets by an ice cutting component within the nugget forming device. The ice nuggets or ice flakes are moves from evaporator 1013 by the auger through ice chute 1012 and lid 1010a to bin 1010 where the ice nuggets or ice flakes are stored prior to being selectively dispensed through dispenser opening 1015.

As an alternative to ozonated water supply 1033, Ice maker and bin assembly 1000 could also use an in-line ozone generator, such as generator 550 of machine 100 or 200. As in those embodiments, assembly 1000 could have an ozone generator in line with potable water supply 1011a, or in-line at a point between reservoir 1011 and evaporator 1013.

In order to eliminate the need for periodic cleaning events, it is possible to use a combination of sealing of the joints and gaps in the boundaries of the foodzone 166 or 1066 and pressurization of the foodzone 166 or 1066 with air or other gas that has been purified by HEPA filtration or other means to remove virtually all of the particulates and organisms from the air or gas. Pressurization serves the purpose to create a continuous flow of clean air from the inside of the foodzone 166 or 1066 to the outside ambient through any remaining gaps in the foodzone 166 or 1066 boundary, thereby preventing the entry of any contamination into the foodzone 166 or 1066 through airborne matter. This approach is well understood through the development of cleanroom systems for medical and manufacturing purposes.

The application of a cleanroom approach to an ice maker with storage and dispensing does not completely solve the challenge of maintaining a sanitary condition within the foodzone 166 or 1066. Potable water must be brought into the ice production mechanism. While this potable water is completely safe for human consumption, it is typically not completely free of live micro-organisms. The water treatment system employed by the municipal water supply, or the private well used, are only required to keep the count of bacteria and other micro-organisms below a level that is known to be safe. Once these live organisms enter the ice maker through the water supply, they are able to establish colonies within the foodzone that multiply over time, and eventually the ice machine must be disinfected to keep the micro-organisms under control.

Through the integration of an automated sanitation process that sterilizes all surfaces and matter within the foodzone 166 or 1066 on a periodic basis, it becomes possible to complete the disinfection required to address micro-organisms that enter through the water supply without disrupting the cleanroom barrier established to prevent entry of airborne contaminants. The challenge faced in implementing an automated sanitation process is achieving complete coverage of all surfaces and fluids within the foodzone 166 or 1066 with the sanitizing agent to achieve the required efficacy, and then removing all traces of the sanitizing agent from the foodzone prior to resuming ice production and dispense. The present disclosure overcomes these challenges through a combination of the sanitizing agent and operation cycle for automated sanitation of a cleanroom foodzone.

The present disclosure utilizes ozone dissolved in water as the sanitizing agent. A key to effective sanitation is achieving the correct combination of concentration for the dissolved ozone in the water, and residence time for contact with the target surfaces and substances in the foodzone 166 or 1066.

Referring back to FIGS. 1-4, ice maker and bin assembly 30 can enter into a sanitizing process during operation. A first step in the sanitizing process includes ice maker 33 being sanitized by metering a known amount of ozone containing water, as shown in FIG. 2 from ozonated water supply 101. Alternatively, as shown in FIG. 3, the amount of ozonated water can come from potable water supply 1 that flows water to ozone generator 550 that generates ozonated water, into sump 3. The ozonated water can also be made at a point between pump 4 and distributor 7, as shown in FIG. 3a. Ozone generator 550 passes incoming potable water through a catalyst, that when energized, splits a fraction of the water molecules in the potable water into hydrogen and oxygen molecules, and then energizes a fraction of the oxygen molecules to produce ozone, which is a radical of the oxygen molecule. The ozone, oxygen that has not been converted into ozone, and hydrogen, are then dissolved back into the potable water stream, providing a water stream that contains dissolved ozone in the range of 0.05 to 3 parts per million (ppm). As shown in FIG. 2, controller 11 can move ozonated water supply valve 101A to an open position allowing a flow of ozonated water into sump 3. As shown in FIG. 3, controller 11 can move water supply valve 1A to an open position and activate ozone generator 550 to generate ozonated water that flows into sump 3.

Controller 11 activates pump 4 to circulate ozonated water from sump 3 to distributor 7, which distributes the ozonated water onto evaporator plate 6. Agitation of the ozonated water over evaporator plate 6 releases some of the ozone from the ozonated water into air in foodzone 166 so that the ozone reacts with undesirable material in the air and on foodzone surfaces in contact with air inside the foodzone to sanitize the air and surfaces. The refrigeration system is not activated so that ice is not formed on evaporator plate 6 and the ozonated water flows from evaporator plate 6 back into sump 3. This cycle continues until a target amount of time in the range from 1 to 10 minutes, or any subranges therebetween, has elapsed. The ozonated water is then drained from sump 3 through drain valve 9 and drain 10.

Alternately, controller 1044 opens drain valve 1019 in ice maker and bin assembly 1000 for a period of time to drain water from evaporator 1013. Controller 1044 then closes drain valve 1019 and controller 1044 moves ozonated water supply valve 1033b to the open position, delivering ozonated water from reservoir 1011 to evaporator 1013. Ozonated water fills evaporator 1013 and reservoir 1011. The ozonated water is in evaporator 1013 and reservoir 1011 until a target amount of time in the range from 1 to 10 minutes, or any subranges therebetween, has elapsed before draining the ozonated water from evaporator 1013. Controller 1044 moves drain valve 1019 to the open position so that ozonated water drains out of evaporator 1013.

The refrigeration system is not operated during this sequence to improve the effectiveness of the ozone in the ozonated water on the evaporator and the water containing surfaces. This ozonated water reacts, for example, with carbon base material, so that the ozone sanitizes the surfaces contacted by the ozonated water, and the ozonated water becomes depleted during this first step; however, some residual ozone may remain in ice maker 33 or ice maker 1005.

After the ozonated water is drained from ice maker 33 or ice maker 1005, a second step in a sanitizing process includes starting an ice making process or the freeze cycle by activating the refrigeration system, and then feeding ozonated water, different from the ozonated water of step one, into sump 3 or reservoir 1011 and evaporator 1013 to produce a target amount of ice. As discussed above, ozone in the ozonated water in step one is depleted upon completion of step one. Accordingly, adding fresh ozonated water that is different than the ozonated water of step one is more effective during step two. As shown in FIG. 2, controller 11 can move ozonated water supply valve 101A to an open position allowing ozonated water to flow into sump 3. As shown in FIG. 3, controller 11 can move water supply valve 1A to an open position and activate ozone generator 550 to generate ozonated water and allow ozonated water to flow into sump 3. As shown in FIG. 3a, controller 11 can control ozone generator 550 to generate ozonated water at a point in the flow stream, into a fluid line between pump 4 and distributor 7. Alternately, as shown in FIG. 6, controller 1044 moves ozonated water supply valve 1033b to the open position delivering ozonated water from reservoir 1011 to evaporator 1013.

Controller 11 activates pump 4 to circulate ozonated water from sump 3 to distributor 7 that distributes the ozonated water onto evaporator plate 6. Agitation of the ozonated water over evaporator plate 6 releases some of the ozone from the ozonated water so that the ozone reacts with undesirable material in the air to sanitize the air. The refrigeration system is activated so that ice is formed on evaporator plate 6 and the ozonated water that does not freeze to evaporator plate 6 flows from evaporator plate 6 back into sump 3. A portion of the ozone in the water remains in the ice formed on evaporator plate 6, and the ice on evaporator plate 6 is harvested into bin 31, as shown in FIG. 1, through ice chute 136, as shown in FIG. 4.

Alternately, ozonated water flows into reservoir 1011 and then into evaporator 1013. The refrigeration system is activated to cool evaporator 1013 in ice maker and bin assembly 1000 during the freeze cycle so that the ice flakes or ice nuggets produced in the evaporator 1013. The auger delivers the ice flakes or ice nuggets through ice chute 1012 and lid 1010a to bin 1010.

The freeze cycle and harvest cycle of ice maker 33 or continuous ice production of ice maker 1005 using ozonated water repeats until a target amount of ice is added to bin 31 or 1010. The amount of ice, or ice flakes, or ice nuggets, containing ozone that is added to bin 31 or bin 1010 is typically in the range of 5% to 20% of a holding capacity of bin 31 or 1010.

Controller 11 then closes ozonated water supply valve 101A, or potable water supply valve 1A and deactivates ozone generator 550, or controller 44 closes ozonated water supply valve 1033b and stops the ice production cycle until a period of time, typically in the range from 1 to 4 hours, is elapsed to allow a sufficient amount of gaseous ozone to be released into the volume of foodzone 166 or 1066 from the ice, or ice flakes, or ice nuggets, outgassing or the ice, or ice flakes, or ice nuggets, melting to ensure effective sanitation of all surfaces that are in contact with air inside foodzone 166 or 1066. As the ice, or ice flakes, or ice nuggets, made with ozonated water melts, ozone is released into the air present in bin 31 or 1010 to react with undesirable material to sanitize the bin. As the ice made with ozonated water outgasses ozone, the ozone is released into the air present in bin 31 or 1010 to react with undesirable material to sanitize the bin. Ice dispenser 35 or 1015 is also operated to cause a small amount of ozone containing ice, or ice flakes, or ice nuggets, to be dispensed, which subjects all passageways within the dispensing subsystem to a combination of gaseous ozone and ozone dissolved in water to react with undesirable material to sanitize these surfaces.

A third step in a sanitizing process includes, a controlled amount of potable water, which has not been treated with ozone, is sprayed by a sprayer 39 that is controlled by a controller 41 over a surface of the ice in bin 31, or a controlled amount of potable water, which has not been treated with ozone, is sprayed by a sprayer 1039 that is controlled by a controller 1041 over a surface of the ice in bin 1010, which serves to melt the remaining ozone containing ice, or ice flakes, or ice nuggets, formed in step two from bin 31 or 1010. This ensures the residual ozone in bin 31 or 1010 is well below the desirable limit, typically less than 0.05 ppm, for ice that will be consumed, and it also carries the melted ozone containing water past the ice, or ice flakes, or ice nuggets, that was in the bin prior to the start of the sanitizing process, sanitizing this ice, or ice flakes, or ice nuggets, by reacting the melted ozone containing water with undesirable material to sanitize the ice, or ice flakes, or ice nuggets, that was in the bin prior to the start of the sanitizing process, and finally providing sanitization of a drain passage 43 or 1043 contained in the machine for handling the melted ozone containing water from the ice storage volume of bin 31 or 1010 by reacting the melted ozone containing water with undesirable material on these surfaces.

After the third step, as shown in FIG. 2, controller 11 closes ozonated water supply valve 101A and opens a potable water supply valve 13A of potable water supply 13, or, as shown in FIGS. 3 and 3a, deactivates ozone generator 550, so that ice maker 33 operates in a non-sanitizing mode or normal operation to form, store and dispense ice formed from potable water, or for ice maker and bin assembly 1000, controller closes ozonated water supply valve 1033b and opens potable water supply valve 1011b so that ice maker 1005 operates in a non-sanitizing mode or normal operation to form, store and dispense ice flakes or ice nuggets formed from potable water.

It is undesirable to have some concentrations of ozone in ice served and consumed by consumers due to taste and/or health concerns. Accordingly, the sanitizing process may be commenced at certain times of the day to minimize concentrations of ozone served to consumers, for example, once a day during the early morning.

It has been determined by the present disclosure that the method and apparatus of the present disclosure provides automatically sanitizing the foodzone of ice maker 33 and dispenser 35 or foodzone 1066 and dispenser 1015 where foodzone 166 or 1066 is either sealed from the surrounding airspace and machine compartments in ice maker and bin assembly 30 or 1000 or is held under positive pressure using air or other gas that is free of particulate matter and micro-organisms. It has been further determined by the present disclosure that the method and apparatus of the present disclosure provides maintaining a sanitary state for foodzone 166 or 1066 without the need to open the foodzone 166 or 1066, and disrupt the protection afforded by the sealing and/or pressurization mechanisms that provide protection against airborne contaminants entering foodzone 166 or 1066.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A method of making ice with an ice maker, the ice maker comprising:
    a refrigeration system;
    an evaporator in operable communication with the refrigeration system;
    a water sump;
    a water pump in communication with the water sump;
    a drain valve in communication with the water sump;
    a potable water line that supplies potable water to the water sump via a potable water supply valve; and
    an ozonated water line that supplies ozonated water to the water sump via an ozonated water supply valve, wherein the potable water supply line and the ozonated water supply line are separate from one another,
the method comprising the steps of:
    controlling the ozonated water line to provide a first volume of ozonated water to the water sump;
    subsequently, controlling the water pump to circulate the first volume of ozonated water from the water sump to the evaporator;
    controlling the water pump to circulate the first volume of ozonated water for a first period of time, to substantially sterilize the ice making unit;
    after the first period of time has elapsed, controlling the water pump to turn off, and controlling the drain valve to drain the first volume ozonated water from the water sump;
    initiating an ozonated-ice making mode via the refrigeration system;
    controlling the ozonated water source to supply a second volume of ozonated water to the water sump;
    subsequently, controlling the water pump to circulate the second volume of ozonated water from the water sump to the ice making unit, thereby forming ozonated ice on the evaporator;
    after the ozonated ice has been formed on the evaporator, initiating an ice harvest mode to remove the ozonated ice from the evaporator and delivering the ice to an ice holding bin; and
    controlling the potable water supply line to supply potable water to the ice holding bin, thereby melting the ozonated ice within the ice holding bin, and releasing ozone so that the ice holding bin is sterilized.

2. The method claim 1, wherein the ice maker further comprises
    a controller,
    wherein the controller controls the potable water supply line, the potable water supply valve, the ozonated water line, the ozonated water supply valve, the drain valve, and the pump.

\* \* \* \* \*